United States Patent [19]

Horimoto

[11] Patent Number: 4,833,011

[45] Date of Patent: May 23, 1989

[54] SYNTHETIC PULP AND ABSORBENT COMPRISING THE SAME

[75] Inventor: Koji Horimoto, Ichihara, Japan

[73] Assignee: Mitsui Petrochemical Industries, Ltd., Chiba, Japan

[21] Appl. No.: 93,773

[22] Filed: Sep. 8, 1987

[30] Foreign Application Priority Data

Sep. 8, 1986 [JP] Japan ................................. 61-209450
Mar. 19, 1987 [JP] Japan ................................... 62-62687

[51] Int. Cl.$^4$ ...................... D21D 3/00; D21F 11/00; D02G 3/00
[52] U.S. Cl. .................................... 428/288; 162/146; 162/157.5; 162/158; 162/164.1; 428/375; 428/392; 428/394; 428/395
[58] Field of Search ............... 428/375, 394, 288, 395 428/392; 162/157.5, 158, 146, 164.1

[56] References Cited

U.S. PATENT DOCUMENTS

| | | | |
|---|---|---|---|
| 3,669,829 | 6/1972 | Caldo et al. | 162/157.5 X |
| 3,808,091 | 4/1974 | Aoki et al. | 162/157.5 |
| 3,848,027 | 11/1974 | Forbess et al. | 162/157.5 X |
| 3,891,499 | 6/1975 | Kato et al. | 162/157.5 |
| 3,950,473 | 4/1976 | Iwahori et al. | 162/157.5 X |
| 4,049,492 | 9/1977 | Lare | 162/157.5 X |
| 4,134,931 | 1/1979 | Hayes, Jr. | 162/157.5 X |
| 4,138,314 | 2/1979 | Patil et al. | 162/157.5 X |
| 4,374,788 | 2/1983 | Gonzales | 162/157.5 X |

*Primary Examiner*—Lorraine T. Kendell
*Attorney, Agent, or Firm*—Sherman and Shalloway

[57] ABSTRACT

A synthetic pulp comprising a pulp fiber of a thermoplastic resin and, adhering to the surface thereof, a polypropylene glycol having a molecular weight of 200 to 10,000, preferably together with a phenolic antioxidant and/or a phosphorous acid ester type antioxidant, has an excellent hydrophilic property even in the dry state and a good wettability or rewettability. This pulp forms a good slurry without bubbling when thrown in water. When a mixture of this synthetic pulp and other hydrophilic short fiber is subjected to a heat-fusion treatment, a fibrous molded articles having an excellent hydrophilic property, a good wettability or rewettability and a high wet strength is obtained, and this fibrous molded article is especially valuable as an absorbent.

17 Claims, No Drawings

SYNTHETIC PULP AND ABSORBENT COMPRISING THE SAME

BACKGROUND OF THE INVENTION

(1) Field of the Invention

The present invention relates to a synthetic pulp having an improved hydrophilic property. More particularly, the present invention relates to a thermoplastic resin synthetic pulp having an excellent wetting property even in the dry state.

Furthermore, the present invention relates to a hydrophilic heat-fusion-bonding synthetic pulp. More specifically, the present invention relates to a hydrophilic heat-fusion-bonding synthetic pulp of a thermoplastic resin, which can partially bond filaments of other fibrous product such as a natural pulp, a natural fiber or a glass fiber by mixing this synthetic pulp with said other fibrous product, forming the mixture into a sheet or other shaped article and subjecting the sheet or the like to a high-temperature heat treatment to melt at least a part of the synthetic pulp, and which has excellent wetting property and hydrophilic property even after the heat-fusion treatment, and also to a fibrous product comprising this synthetic pulp.

(2) Description of the Prior Art

A so-called synthetic pulp formed from a thermoplastic resin as the starting material is known. For example, Japanese Patent Publication No. 47049/77 discloses a process for the preparation of a pulp product which comprises discharging a high-temperature high-pressure dispersion of a polyolefin in a hydrocarbon solvent and water in a reduced pressure zone to effect flash spinning and obtain a dispersion of a polyolefin fibrous substance in water and beating or refining the fibrous substance.

This synthetic pulp is hydrophobic and has no water-absorbing property. It is known that in order to impart wetting and water-absorbing properties to this synthetic pulp, the surface treatment is carried out by incorporating polyvinyl alcohol or non-ionic surface active agent into the synthetic pulp.

However, a polyolefin type synthetic pulp surface-treated with polyvinyl alcohol shows a dispersibility when immersed in water, but in the dry state, the synthetic pulp shows a water-repellent property and does not show a wetting or water-absorbing property.

Moreover, a synthetic pulp surface-treated with a non-ionic surface active agent is defective in that if a surface active agent having a large HLB value is used, although the synthetic pulp has a wetting property, bubbling is violent at the time of wetting, and that if a surface active agent having a small HLB value is used, the wetting property is insufficient.

Furthermore, the synthetic pulp surface-treated with a surface active agent is defective in that if the synthetic pulp is mixed with other fibrous product such as a natural pulp, a natural fiber or glass fiber and subjected to a high-temperature heat treatment to melt the synthetic pulp and partially bond filaments of the fibrous product to one another, the surface active agent adhering to the synthetic pulp is oxidized and decomposed and the hydrophilic property given to the synthetic pulp by the surface treatment with the surface active agent is lost. Even if the non-surface-treated syntheic pulp is mixed with other fibrous product and a product obtained by partially fusion-bonding filaments of the fibrous product to one another through the synthetic pulp is surface-treated with a surface active agent for overcoming the above-mentioned defect, it is difficult to effectively treat only the synthetic pulp.

The foregoing problems are included in not only synthetic pulps as described above but also other various fibrous products of thermoplastic resins.

SUMMARY OF THE INVENTION

It is therefore a primary object of the present invention to provide a synthetic pulp which shows an excellent hydrophilic property and a good wettability or rewettability even in the dry state and gives a good slurry with controlled bubbling when wetted with water or thrown into water.

Another object of the present invention is to provide a hydrophilic heat-fusion-bonding pulp in which the hydrophilic property or the wettability or rewettability is not substantially degraded even if the synthetic pulp is molten to bond filaments of other fibrous product such as a natural pulp, a natural fiber or a glass fiber by mixing the synthetic pulp with said other fibrous product and subjecting the mixture to a heat treatment at a high temperature to partially melt the synthetic pulp.

Still another object of the present invention is to provide a fibrous molded article, especially an absorbent, which has a high wet strength and is excellent in hydrophilic and wetting characteristics.

In accordance with one aspect of the present invention, there is provided a synthetic pulp having an improved hydrophilic property, which comprises a pulp fiber of a thermoplastic resin and a polypropylene glycol having a molecular weight of 200 to 10,000, which adheres to the surface of the fiber.

In accordance with another aspect of the present invention, there is provided a synthetic pulp having an improved hydrophilic property, which comprises a pulp fiber of a thermoplastic resin and, adhering to the surface of the fiber, a composition comprising (i) a polypropylene glycol having a molecular weight of 200 to 10,000 and (ii) at least one stabilizer selected from the group consisting of phenolic antioxidants and phosphorous acid ester type antioxidants.

In accordance with still another aspect of the present invention, there are provided a fibrous molded article composed of a paper-made mixture comprising 5 to 50% by weight of a pulp fiber of a thermoplastic resin and 50 to 95% by weight of other hydrophilic short fiber, filaments of said other hydrophilic short fiber being at least partially bonded to one another through the fusion-treated thermoplastic resin pulp fiber, wherein the thermoplastic resin pulp fiber has on the surface thereof a composition comprising (I) a polypropylene glycol having a molecular weight of 200 to 10,000 and (II) at least one stabilizer selected from the group consisting of phenolic antioxidants and phosphorous acid ester type antioxidants, and an absorbent formed of this fibrous molded article.

DETAILED DESCRIPTION OF THE PREFERRED EMBODIMENTS

The synthetic pulp of the present invention shows an excellent hydrophilic property and a good wettability or rewettability even in the dry state, and when the synthetic pulp is wetted with water or is slurried in water, bubbling is not substantially caused, and a good slurry comprising the uniformly dispersed synthetic pulp can be obtained.

It is known that a polypropylene glycol having a molecular weight of 200 to 10,000 can be used as a surface active agent. A synthetic pulp having a polyethylene glycol, which is an analogous compound known as a surface active agent, adhering to the surface thereof, has no substantial hydrophilic property, and if a synthetic pulp is surface-treated with other surface active agent, the hydrophilic property is improved but the surface-treated synthetic pulp is defective in that bubbling is violent when slurried in water. Accordingly, the synthetic pulp of the present invention, which is improved in the hydrophilic property and which gives a good slurry without any substantial bubbling when slurried in water, exerts a prominently excellent unexpected effect.

It is obvious that the improvement of the hydrophilic property or the wettability or rewettability in the present invention is due not only to the utilization of the specific property of an ordinary surface active agent but also to a special effect by a specific combination of a pulp fiber of a thermoplastic resin and a polypropylene glycol having a specific molecular weight.

Furthermore, when a pulp fiber of a thermoplastic resin having only a polypropylene glycol adhering to the surface thereof is subjected to a heat treatment at such a high temperature as causing melting of the pulp fiber, the hydrophilic property or the wettability or rewettability tends to decrease. In contrast, since a specific stabilizer and a polypropylene glycol having a specific molecular weight adhere in combination to the surface of the synthetic pulp of the present invention, even after the synthetic pulp is subjected to a heat treatment at such a high temperature as causing fusion bonding in at least a part of the pulp fiber (about 180° to about 300° C.), the effect of imparting the hydrophilic property and the wettability or rewettability to the synthetic pulp by the polypropylene glycol is not substantially reduced. This is a prominently excellent effect attained by the present invention.

The present invention will now be described in detail.

SYNTHETIC PULP FIBER

As the fiber of a thermoplastic resin used in the present invention, there can be mentioned a short fiber obtained by melt-spinning a thermoplastic resin and cutting the spun fiber into a predetermined length, a pulp fiber obtained by flash-spinning a solution or emulsion of a thermoplastic resin, a fibrilated short fiber obtained by disintegrating and cutting a drawn film of a thermoplastic resin, a fiber obtained by composite-melt-spinning at least two thermoplastic resins differing in the melting point and disintegrating and cutting the spun fiber, and analogues thereof.

As the thermoplastic resin, there can be mentioned polyolefins, polyesters, polyacrylonitrile and other hydrophobic thermoplastic resins. Crystalline olefin polymers, for example, polyethylene, polypropylene and copolymers of ethylene with at least one α-olefin, such as an ethylene/propylene copolymer, an ethylene-1-butene copolymer and an ethylene/4-methyl-1-pentene copolymer, are especially preferred because a fusion-bonding treatment of a paper-made product of the fiber can be carried out at a relatively low temperature and the wet strength of the fibrous molded article is relatively high. In view of the easiness of the fusion-bonding treatment, it is preferred that the melting point of the pulp fiber be 70° to 250° C., especially 90° to 180° C. A polyolefin pulp fiber is defective in that it is poor in the hydrophilic property and the wettability, but these properties are prominently improved according to the present invention.

The process for preparing a pulp fiber from a thermoplastic resin is known, and any of thermoplastic resin pulp fibers prepared according to various known processes can be used in the present invention but a polyolefin pulp fiber prepared by flash-spinning a solution or emulsion of a polyolefin is preferred. It is preferred that the fiber or pulpy substance should have a specific surface area of at least 0.1 m$^2$/g.

A pulp fiber used most preferably in the present invention is composed of polyethylene or polypropylene multi-branched filaments having an average length of 0.1 to 10 mm, especially 0.5 to 5 mm, and the density of this pulp fiber is 0.900 to 0.980 g/cm$^3$ (as determined according to the method of ASTM D-1505).

The pulp fiber of this type is obtained by flash-spinning a dispersion comprising a crystalline polyolefin, an organic solvent for the polyolefin and water, in which water is present in the form of a dispersion medium and the polyolefin and organic solvent form a dispersed phase, under such temperature and pressure conditions that substantially all of the organic solvent is evaporated but water is not substantially evaporated, and beating or refining the spun fiber. Generally, polyvinyl alcohol is stuck on the surface of the fiber in an amount of 0.01 to 10% by weight based on the fiber so as to improve the water dispersibility of the pulp fiber at the beating or refining step. This can be accomplished by incorporating an aqueous solution of the polyvinyl alcohol in the dispersed phase of the above-mentioned dispersion or by coating the flash-spun fiber with an aqueous solution of the polyvinyl alcohol, drying the fiber if necessary and beating or refining the fiber.

TREATMENT

The polypropylene glycol used for the treatment of the present invention is obtained by polymerizing propylene oxide according to customary procedures, and the molecular weight is 200 to 10,000, preferably 400 to 6,000.

The molecular weight of the polypropylene glycol (PPG) referred to herein is the value determined by the gel permeation chromatography (GPC), but the molecular weight can be calculated by comparing the OH value of sample PPG with that of reference PPG having a known OH value. If the molecular weight of the polypropylene glycol is too low and below the above-mentioned range, the adhering property to the pulp fiber is degraded, and if the molecular weight of the polypropylene glycol is too high, the effect of imparting the hydrophilic property is lowered.

It is preferred that the amount of the polypropylene stuck to the pulp fiber be 0.01 to 10% by weight, especially 0.05 to 5% by weight, based on the pulp fiber. If the amount of the polypropylene glycol is too small and below this range, no substantial effect of improving the hydrophilic property or the wettability or rewettability of the pulp fiber can be attained. If the amount of the polypropylene glycol is too large and exceeds the above-mentioned range, the performance of the pulp fiber as the synthetic pulp is degraded.

In accordance with a preferred embodiment of the present invention, the above-mentioned polypropylene glycol is used in combination with at least one heat stabilizer selected from the group consisting of phenolic antioxidants and phosphorous acid ester type antioxidants as the fiber surface-treating agent.

Known phenolic antioxidants can be used. However, in view of the heat stabilizing effect and the compatibility with the polypropylene glycol, a styrenated phenol represented by the following formula (I):

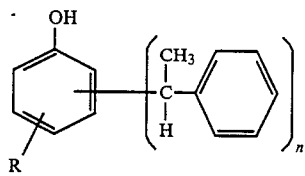
(I)

wherein R stands for a hydrogen atom or an alkyl group having 1 to 10 carbon atoms and n is an integer of from 1 to 3, is preferred.

This styrenated phenol includes mono-($\alpha$-methylbenzyl)phenol, di-($\alpha$-methylbenzyl)phenol, tri-($\alpha$-methylbenzyl)phenols and mixtures comprising at least two of these phenols. In the above formula (I), the $\alpha$-methylbenzyl group is generally attached to the ortho- or para-position to the phenolic hydroxyl group.

Various known phosphorous acid ester type antioxidants can be used. However, in view of the heat stabilizing effect and the compatibility with the polypropylene glycol, a trialkyl or triaryl phosphite represented by the following formula (II):

(II)

wherein R' stands for an alkyl group having 10 to 20 carbon atom or an aryl group represented by the following formula (III):

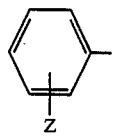
(III)

in which Z stands for a hydrogen atom or an alkyl group having 1 to 20 carbon atoms, is preferred. As especially preferred examples of the phosphorous acid ester type antioxidant, there can be mentioned tridecyl phosphite, trioctadecyl phosphite, tristearyl phosphite, triphenyl phosphite and tris(nonylphenyl) phosphite.

The foregoing heat stabilizers may be used singly or in the mixtures of two or more of them. Especially, if the above-mentioned phenolic antioxidant and the phosphorous acid ester type antioxidant are used in combination, the effect of maintaining a high hydrophilic property or a good wettability or rewettability in the pulp fiber of the present invention even after heat-fusion-bonding can be further improved. Of course, the heat stabilizer exerts a function of preventing thermal deterioration of the polypropylene glycol at the heat-fusion-bonding treatment. Furthermore, the heat stabilizer advantageously exerts a function of preventing thermal deterioration, such as scorching, of the pulp fiber of a thermoplastic resin such as polyethylene or other fiber mixed with the pulp fiber, such as a natural pulp.

In the above-mentioned preferred embodiment of the present invention, the polypropylene glycol is used in the above-mentioned amount, and it is preferred that the heat stabilizer be used in an amount of 0.001 to 10% by weight, especially 0.01 to 5.0% by weight, based on the pulp fiber. If the amount of the heat stabilizer is too small and below the above-mentioned range, the effect of preventing thermal deterioration of the polypropylene glycol or the pulp fiber of the thermoplastic resin is insufficient and the hydrophilic property is reduced when the pulp fiber is subjected to the heat-fusion-bonding treatment. If the amount stuck of the heat stabilizer exceeds the above-mentioned range, the effect of imparting a hydrophilic property by the polypropylene glycol tends to decrease.

The method for applying the polypropylene glycol or the composition comprising the polypropylene glycol and the heat stabilizer to the surface of the pulp fiber is not particularly critical, but optional means can be adopted. For example, there can be mentioned (1) a method in which the polypropylene glycol or its mixture with the heat stabilizer, or an aqueous solution or dispersion thereof is sprayed to the pulp fiber, (2) a method in which the pulp fiber is immersed in the polypropylene glycol or its mixture with the heat stabilizer, or an aqueous solution or dispersion thereof, and (3) a method in which the polypropylene glycol or its mixture with the heat stabilizer, or an aqueous solution or dispersion thereof is added to an aqueous slurry of the pulp fiber. The methods (2) and (3) are preferred because the polypropylene glycol or its mixture with the heat stabilizer is sufficiently adsorbed and stuck on the surface of the pulp fiber during stirring and mixing in an aqueous solution or aqueous dispersion. The method (3) is especially preferred because the respective components are uniformly adsorbed and stuck in desired amounts. The temperature adopted for adsorbing and sticking the polypropylene glycol or its mixture with the heat stabilizer on the surface of the pulp fiber is generally 0° to 90° C., and room temperature is preferred.

After the polypropylene glycol or its mixture with the heat stabilizer has been adsorbed and stuck on the pulp fiber, the treated pulp fiber is dehydrated according to customary procedures and is dried according to need, whereby the hydrophilic heat-fusion-bonding pulp fiber of the present invention can be obtained.

USE

The synthetic pulp can be used in the fields where synthetic pulps have been used. For example, the synthetic pulp of the present invention can be used as a wood pulp substitute, a material for a non-woven fabric, an aqueous liquid-absorbing material, an oil-absorbing material, an insulating material and the like.

By mixing the pulp fiber of the present invention with a natural pulp, a natural fiber, a semi-synthetic fiber, an organic fiber such as a synthetic fiber having a melting point higher than that of the pulp fiber of the present invention or an inorganic fiber such as a glass fiber, making a formed body having an optional shape, such as a sheet, and subjecting the formed body to a fusion-bonding treatment at such a high temperature that at least a part of the synthetic pulp fiber of the present invention is molten, there is obtained a fibrous molded article in which filaments of other hydrophilic short fiber are bonded at least partially to one another through the fusion-treated thermoplastic resin pulp fiber. This fibrous molded article is excellent in the hydrophilic property and the wettability or rewettability and is characterized in that the wet strength is high.

In the fibrous molded article, it is preferred that the weight ratio of the hydrophilic heat-fusion-bonding synthetic pulp fiber to other hydrophilic short fiber be in the range of from 5/95 to 50/50, especially from 10/90 to 45/55. If the amount used of the synthetic pulp fiber is smaller than 5% by weight, the mechanical strength, especially the wet strength, is hardly improved by the fusion-bonding treatment. The mixture can be molded by either the wet method or the dry method.

An air oven, an infrared ray heater or the like is generally used for the fusion-bonding treatment of the thermoplastic resin pulp fiber. The heating temperature depends on the kind of the thermoplastic resin constituting the pulp fiber, but it is preferred that the heating temperature be in the range of from the melting point of the thermoplastic resin used to a temperature higher by about 100° C. than the melting point of the thermoplastic resin used.

The fibrous molded article of the present invention is ordinarily in the form of a web, and the bulk specific gravity can be adjusted to some extent by the fusion-bonding treatment of the thermoplastic resin pulp fiber but products having a desired bulk specific gravity can be obtained by performing a pressing treatment simultaneously with the fusion-bonding treatment according to need.

The fibrous molded article of the present invention can be used for the production of paper products such as embossed paper, heat-sealing paper, water-resistant paper, electrical paper, forming paper and agricultural paper, various non-woven fabric products, sanitary products, construction materials and forming boards. When a wood pulp fiber is used as other hydrophilic short fiber, the fibrous molded article of the present invention can be valuably used as various absorbent materials such as throw-away diapers, sanitary napkins, medical sponges, wound pads and towels.

The present invention will now be described in detail with reference to the following examples that by no means limit the scope of the invention.

EXAMPLE 1

To 10 l of water was added 100 g of a multi-branched pulp fiber prepared from polyethylene (SWP® E400 supplied by Mitsui Petrochemical Industries), which had a density of 0.96 g/cc, a melting point of 132° C., an average fiber length of 0.9 mm and a freeness of 500 CSF and 1.0 g of a polypropylene glycol having a molecular weight of 2,000 (supplied by Wako Junyaku) was further added. The composition was charged into a household mixer dividedly in several times and violently stirred at room temperature for 30 seconds to stick the polypropylene glycol to the pulp fiber.

The stirred composition was dehydrated and molded by a square sheet machine of 25 cm×25 cm and further dehydrated by a hand press to form a sheet having a water content of 50% by weight and a bond dry basis weight of 1,500 g/m². The sheet was dried at 50° C. for 8 hours by a circulation type dried to form a dry sheet in the bone dry state.

Water maintained at 20° ±2° C. was dropped on the surface of the dry sheet. Water was immediately absorbed in the sheet.

When the dry sheet was pulverized by a hammer mill type pulverizer, the obtained fluffy product was added to water maintained at 20° ±2° C. at a concentration of 10 g/l and the resulting composition was quitely stirred, a homogeneous slurry was obtained. Clods were removed from the slurry by an 8-cut screen. It was found that the content of such clods was lower than 10 ppm and the slurry had a good dispersion state.

COMPARATIVE EXAMPLE 1

A dry sheet was prepared in the same manner as described in Example 1 except that the pulp fiber (SWP® E400) used was directly treated without sticking the polypropylene glycol thereto. When water maintained at 20° ±2° C. was dropped on the sheet, water drop were not absorbed in the sheet but were left on the sheet surface.

COMPARATIVE EXAMPLE 2

A dry sheet was prepared in the same manner as described in Example 1 except that 1.0 g of POE nonylphenyl ether (Emulgen 910 supplied by Kao, HLB=12.2) as a non-ionic surface active agent was used instead of the polypropylene glycol.

Although this sheet absorbed water, bubbling was violent when the pulverized fluffy product was thrown into water and the mixture was stirred, and no good slurry was obtained.

COMPARATIVE EXAMPLE 3

A dry sheet was prepared in the same manner as described in Example 1 except that 1.0 g of a polyethylene glycol having a molecular weight of 2,000 (supplied by Wako Junyaku) was used instead of the polypropylene glycol.

When water maintained at 20±2° C. was dropped on the dry sheet, water drops were not absorbed in the sheet.

EXAMPLE 2

To 10 l of water was added 100 g of a multi-branched pulp fiber prepared from polyethylene having a polyvinyl alcohol content of 1.1% by weight (SWP® E400 supplied by Mitsui Petrochemical Industries), and 1.0 g of a polypropylene glycol having a molecular weight of 2,000 (PPG-2000 supplied by Wako Junyaku) and 0.2 g of mono-di- or tri(α-methylbenzyl)phenol (Nocrak SP supplied by Ouchi Shinko Kagaku Kogyo) were further added. The composition was violently stirred at room temperature for 30 seconds to stick the polypropylene glycol and Nocrak SP to the pulp fiber.

The stirred composition was dehydrated and molded by a square sheet machine of 25 cm×25 cm and was further dehydrated by a hand press to obtain a synthetic pulp sheet having a water content of 50% by weight and a bone dry basis weight of 1,500 g/m². It was found that more than 90% of the used polypropylene glycol and Nocrak SP were stuck to the pulp fiber.

EXAMPLE 3

(Preparation of Test Sample)

Water was added to a mixture comprising 78 parts by weight of a glass micro-fiber (Code 106 supplied by Johns-Manville) and 22 parts by weight of the pulp fiber used in Example 2 so that the concentration of the mixture in the slurry was 5 g/l. The composition was stirred for 30 seconds in a JIS type pulper to form an aqueous slurry.

The obtained slurry was dehydrated and molded by a square sheet machine of 25 cm×25 cm and dried at room temperature to obtain a fibrous sheet having a basis weight of 100 g/m².

The fibrous sheet was heat-treated at a temperature shown in Table 1 in a hot air-circulating type drier and the hydrophilic property was measured. The obtained results are shown in Table 1.

Incidentally, the hydrophilic property of the sheet heat-treated at 140° C., that was insufficient for effecting heat-fusion-bonding, was similarly tested, and the obtained results are shown in Table 1. (Hydrophilic Property Test)

On the test sheet was dropped 1 cm³ of water maintained at 20° ±2° C., and the time required for complete absorption of water in the sheet was measured.

EXAMPLE 4

(Preparation of Test Sample)

A fibrous sheet having a basis weight of 300 g/m² was prepared in the same manner as described in Example 3 except that a wood pulp (NBSP supplied by Sanyo Kokusaku Pulp) was used instead of the glass microfiber and the concentration of the mixture in the slurry was changed to 10 g/l.

The sheet was heat-treated in the same manner as described in Example 3, and the hydrophilic property of the obtained sheet was measured. The obtained results are shown in Table 2. Incidentally, the hydrophilic property of the sheet heat-treated at 140° C. was similarly tested. The obtained results are shown in Table 2.

EXAMPLE 5

A synthetic pulp sheet was prepared in the same manner as described in Example 2 except that tristearyl phosphite $(C_{18}H_{37}O)_3P$ was used instead of Nocrak SP.

EXAMPLE 6

A fusion-bonded fibrous sheet was prepared in the same manner as described in Example 3 except that the synthetic pulp obtained in Example 5 was used instead of the synthetic pulp obtained in Example 2. The obtained results are shown in Table 1.

EXAMPLE 7

A fusion-bonded fibrous sheet was prepared in the same manner as described in Example 4 except that the synthetic pulp obtained in Example 5 was used instead of the synthetic pulp obtained in Example 2. The obtained results are shown in Table 2.

COMPARATIVE EXAMPLE 4 THROUGH 7

Synthetic pulps were prepared in the same manner as described in Example 2 except that substances shown in Table 3 were used as the hydrophilic property-imparting agent instead of the mixture of the polypropylene glycol and Nocrak SP.

COMPARATIVE EXAMPLES 8 THROUGH 11

Fusion-bonded fibrous sheets were prepared in the same manner as described in Example 3 except that the synthetic pulps obtained in Comparative Examples 4 through 7 were used instead of the synthetic pulp obtained in Example 2. The obtained results are shown in Table 1.

COMPARATIVE EXAMPLE 12 AND 13

Fusion-bonded fibrous sheets were prepared in the same manner as described in Example 4 except that the synthetic pulps obtained in Comparative Examples 4 and 6 were used instead of the synthetic pulp obtained in Example 2. The obtained results are shown in Table 2.

EXAMPLE 8

Pulp fibers having a polypropylene glycol and a heat stabilizer, adhering to the surface thereof, were prepared in the same manner as described in Example 2 except that the amount added of Nocrak SP (heat stabilizer) was changed to 0.01 g (sample 1). 0.02 g (sample 2), 0.5 g (sample 3) or 0.1 g (sample 4).

Sheets were prepared in the same manner as described in Example 3 by using the so-obtained pulp sheets, and the hydrophilic properties of these sheets were measured. The obtained results are shown in Table 4.

TABLE 1

| | Hydrophilic Property (water absorption time, seconds) | | | |
| --- | --- | --- | --- | --- |
| | Heat Treatment Temperature (°C.) | | | |
| | 140 | 180 | 190 | 200 |
| Example 3 | 5.0 | 5.1 | 4.4 | 11.8 |
| Example 6 | 5.1 | 5.3 | 6.5 | 30.2 |
| Comparative Example 8 | 4.8 | 5.9 | 11.3 | above 180 |
| Comparative Example 9 | 5.3 | 5.6 | 7.8 | above 180 |
| Comparative Example 10 | 4.7 | 7.5 | above 180 | above 180 |
| Comparative Example 11 | 5.1 | 7.3 | above 180 | above 180 |

TABLE 2

| | Hydrophilic Property (water absorption time, seconds) | | | |
| --- | --- | --- | --- | --- |
| | Heat Treatment Temperature (°C.) | | | |
| | 140 | 180 | 190 | 200 |
| Example 4 | 7.3 | 7.4 | 8.4 | 15.0 |
| Example 7 | 7.5 | 7.6 | 12.3 | 51.2 |
| Comparative Example 12 | 7.2 | 8.3 | 31.5 | above 180 |
| Comparative Example 13 | 5.6 | above 180 | above 180 | above 180 |

TABLE 3

| Comparative Example No. | Hydrophilic Property-Imparting Agent |
| --- | --- |
| 4 | PPG-2000 (no heat stabilizer) |
| 5 | PPG-3000[1] (no heat stabilizer) |
| 6 | Emulgen 910[2] |
| 7 | Emulgen 910/Nocrak SP (1.0/0.2) |

Note
[1]Polypropylene glycol having a molecular weight of 3,000 (supplied by Wako Junyaku)
[2]POE nonylphenyl ether (supplied by Kao)

TABLE 4

| | Hydrophilic Property (water absorption time, seconds) | |
| --- | --- | --- |
| | Heat Treatment Temperature (°C.) | |
| | 190 | 200 |
| sample 1 | 7.1 | 60 |
| sample 2 | 7.0 | 24.0 |
| sample 3 | 7.5 | 8.9 |
| sample 4 | 6.7 | 9.1 |

I claim:

1. A synthetic pulp having an improved hydrophilic property, which comprises pulp fibers of a thermoplastic resin and from 0.01 to 10% by weight, based on the pulp fibers, of a polypropylene glycol having a molecular weight of 200 to 10,000, which adheres to the surface of the fibers.

2. A synthetic pulp as set forth in claim 1, wherein the thermoplastic resin is a crystalline polyolefin.

3. A synthetic pulp as set forth in claim 1, wherein the thermoplastic resin is polyethylene or polypropylene.

4. A synthetic pulp as set forth in claim 1, wherein the pulp fibers are multi-branched polyethylene or polypropylene fibers having an average fiber length of 0.1 to 10 mm.

5. A synthetic pulp as set forth in claim 1, wherein the pulp fibers are multi-branched polyethylene or polypropylene fibers having 0.01 to 10% by weight of polyvinyl alcohol on the surface thereof.

6. A synthetic pulp as set forth in claim 1, wherein the pulp fibers are pulp fibers obtained by flash-spinning a dispersion comprising a crystalline polyolefin, an organic solvent for the polyolefin and water, in which water is present as the dispersing medium and the polyolefin and organic solvent are present as the dispersed phase, under such temperature and pressure conditions that substantially all of the organic solvent is evaporated and water is not substantially evaporated, and heating or refining the spun fibers.

7. A synthetic pulp as set forth in claim 6, wherein the dispersion medium of the dispersion contains polyvinyl alcohol therein.

8. A synthetic pulp as set forth in claim 6, wherein the pulp fibers are pulp fibers obtained by mixing said spun fibers with polyvinyl alcohol and beating or refining the mixture.

9. A synthetic pulp as set forth in claim 1, wherein the polypropylene glycol has a molecular weight of 400 to 6,000.

10. A synthetic pulp as set forth in claim 1, wherein the polypropylene glycol is present in an amount of 0.05 to 5% by weight based on the pulp fibers.

11. A synthetic pulp having an improved hydrophilic property, which comprises pulp fibers of a thermoplastic resin, and adhering to the surface of the fibers, a composition comprising (i) from 0.01 to 10% by weight, based on the fibers, of a polypropylene glycol having a molecular weight of 200 to 10,000 and (ii) from 0.001 to 10% by weight, based on the weight of the fibers of at least one stabilizer selected from the group consisting of phenolic antioxidants and phosphorus acid ester type antioxidants.

12. A synthetic pulp as set forth in claim 11, wherein (ii) comprises a phenolic antioxidant which is a styrenated phenol represented by the following formula (I):

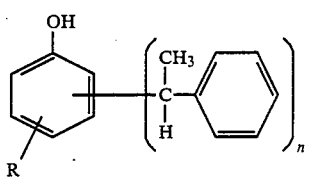

wherein R stands for a hydrogen atom or an alkyl group having 1 to 10 carbon atoms and n is an integer of from 1 to 3.

13. A synthetic pulp as set forth in claim 11, wherein (ii) comprises a phosphorous acid ester type antioxidant which is a trialkyl or triaryl phosphite represented by the following formula (II):

wherein R' stands for an alkyl group having 10 to 20 carbon atoms or an aryl group represented by the following formula (III):

in which Z stands for a hydrogen atom or an alkyl group having 1 to 20 carbon atoms.

14. A synthetic pulp as set forth in claim 11, wherein the pulp fibers are multi-branched polyethylene fibers having 0.01 to 10% by weight of polyvinyl alcohol on the surface thereof.

15. A fibrous molded article composed of a paper-made mixture comprising 5 to 50% by weight of pulp fibers of a thermoplastic resin and 50 to 95% by weight of other hydrophilic short fibers, said other hydrophilic short fibers being at least partially bonded to one another through the fusion-treated thermoplastic resin pulp fibers, wherein the thermoplastic resin pulp fibers have on the surface thereof a composition comprising (I) from 0.01 to 10% by weight of the fibers of a polypropylene glycol having a molecular weight of 200 to 10,000 and (II) from 0.001 to 10% by weight of the fiber of at least one stabilizer selected from the group consisting of phenolic antioxidants and phosphorus acid ester type antioxidants.

16. A fibrous molded article as set forth in claim 15, wherein said other hydrophilic short fibers are natural pulp fibers, natural fibers or glass fibers.

17. A fibrous molded article as set forth in claim 15, wherein said other hydrophilic short fibers are natural pulp fibers.

* * * * *